(12) United States Patent
Gomez-Llorens

(10) Patent No.: US 10,687,944 B2
(45) Date of Patent: Jun. 23, 2020

(54) PENIS IMPLANT, PARTICULARLY FOR FEMALE-TO-MALE TRANSSEXUAL

(71) Applicant: ZEPHYR SURGICAL IMPLANTS, Saint-Brice-Courcelles (FR)

(72) Inventor: Christophe Gomez-Llorens, Saint-Brice-Courcelles (FR)

(73) Assignee: ZEPHYR SURGICAL IMPLANTS, Saint-Brice-Courcelles (FR)

( * ) Notice: Subject to any disclaimer, the term of this patent is extended or adjusted under 35 U.S.C. 154(b) by 194 days.

(21) Appl. No.: 15/742,894

(22) PCT Filed: Jul. 13, 2016

(86) PCT No.: PCT/FR2016/051809
§ 371 (c)(1),
(2) Date: Jan. 9, 2018

(87) PCT Pub. No.: WO2017/009580
PCT Pub. Date: Jan. 19, 2017

(65) Prior Publication Data
US 2018/0200060 A1    Jul. 19, 2018

(30) Foreign Application Priority Data
Jul. 16, 2015   (FR) ...................................... 15 56692

(51) Int. Cl.
*A61F 2/26*   (2006.01)
*A61F 5/41*   (2006.01)
*A61F 2/00*   (2006.01)

(52) U.S. Cl.
CPC ................. *A61F 2/26* (2013.01); *A61F 5/41* (2013.01); *A61F 2/0063* (2013.01); *A61F 2005/414* (2013.01)

(58) Field of Classification Search
CPC .. A61F 2/26; A61F 2250/00; A61F 2250/001; A61F 2250/0012
(Continued)

(56) References Cited

U.S. PATENT DOCUMENTS 6,475,137 B1    11/2002 Elist
2005/0014993 A1*   1/2005 Mische ..................... A61F 2/26
600/40

(Continued)

FOREIGN PATENT DOCUMENTS

WO        96/34211 A1    10/1996
WO      03/103537 A2    12/2003
WO    2006/096001 A1     9/2006

OTHER PUBLICATIONS

Prosthetics in Female to Male Transgender, Lee C. Zhao, Nov. 2016, 23 pages, NYU School of Medicine. (Year: 2016).*

(Continued)

*Primary Examiner* — Samuel G Gilbert
(74) *Attorney, Agent, or Firm* — Ladas & Parry LLP; Malcolm J. MacDonald

(57) ABSTRACT

A penile implant having an elongate erectile body (2) supported by a symphyseal anchoring mount (3). The symphyseal anchoring mount (3) has a mounting plate (25) presenting a bearing face (26) extending in a plane, and the erectile body (2) extends from the face opposite the bearing face, in a direction that forms with the plane of the bearing face, an angle of inclination lying in the range 5° to 30°, and preferably in the range 10° to 20°, the erectile body (2) having at its end that is opposite the end provided with the symphyseal anchoring mount, a bulbous portion (4) forming a glans.

10 Claims, 2 Drawing Sheets

(58) Field of Classification Search
USPC .......................................................... 600/40
See application file for complete search history.

(56) References Cited

U.S. PATENT DOCUMENTS

| | | | | |
|---|---|---|---|---|
| 2008/0139880 A1* | 6/2008 | Choi | .................. | A61F 2/26 |
| | | | | 600/40 |
| 2008/0195178 A1* | 8/2008 | Kuzma | .................. | A61N 1/375 |
| | | | | 607/57 |
| 2012/0109333 A1* | 5/2012 | Forsell | .................. | A61F 2/3603 |
| | | | | 623/23.11 |

OTHER PUBLICATIONS

International Search Report for Application No. PCT/FR2016/051809, dated Sep. 14, 2016; French Search Report for French Application No. 1556692, dated Dec. 9, 2015.

* cited by examiner

PENIS IMPLANT, PARTICULARLY FOR FEMALE-TO-MALE TRANSSEXUAL

The present invention relates to the technical field of penile implants for creating an erection for a female to male (FTM) transsexual, having undergone phalloplasty.

In known manner, phalloplasty is a plastic surgery operation with the aim of constructing a neo-penis and a neo-urethra. To this end, the surgeon makes the neo-penis from a flap of rolled up skin that has previously been taken in particular from the forearm, thigh, or side of the chest of the person. The surgeon makes the neo-urethra, which is anastomosed to the female urethra, in the same way.

In order to create an erection, such a neo-penis must include an erectile body. To this end, the surgeon fixes the erectile body on the pubic symphysis of the person. A first solution consists in fixing as the erectile body, a malleable body, directly on the pubic symphysis. The malleable body is generally made of silicone and is fastened by means of a suture anchored directly in the pubic symphysis. Over time, the suture shears through the malleable body leading to deterioration and eventually to destruction of the prosthesis.

A second solution consists in fixing as the erectile body, an inflatable body connected by a hydraulic circuit to a pump. In order to avoid piercing the inflatable body during fixing of the implant, the surgeon uses a tube of tissue to make a sleeve into which the inflatable body is inserted. The implant is fastened on the pubic symphysis by means of sutures passing through the sleeve and being anchored in the pubic symphysis. Over time, as the penile implant is subjected to stress, the inflatable body detaches from the sleeve, leading to destruction of the implant.

There is also known from patent application WO 2006/096001 an implant for a penis including a symphyseal anchoring mount with a mounting plate presenting a curved bearing face. The symphyseal anchoring mount supports an erectile body extending from the face opposite the bearing face. The erectile body is connected to a reservoir and a pump that makes it possible to inflate it.

That implant does not constitute a penile implant as such, since it is intended to be inserted inside a person's penis to restore erectile function or to increase penis size. That implant, which is placed under the skin between the corpora cavernosa constitutes an erectile prosthesis or a stiffener rod, but not a prosthesis for simulating the body and volume of a penis.

In addition, U.S. Pat. No. 6,475,137 describes an implant for a penis including a symphyseal anchoring mount comprising a body for receiving an erectile body connected to a reservoir and to a pump making to possible to inflate it. That receiving body is for being fastened to a mounting base portion on a person's pelvis.

That implant is designed for biological men and makes use of the corpora cavernosa to provide filling by being positioned underneath the skin and around the corpora cavernosa. That implant does not constitute a penile implant as such, since it is intended to be inserted inside a person's penis to restore erectile function.

The analysis of the prior art shows that there exists no female-to-male transsexual penile implant presenting all of the anatomical characteristics of a penis and that is reliable over time.

The present invention thus aims to overcome the drawbacks of the prior art by providing a female-to-male transsexual penile implant designed to withstand the various mechanical stresses it receives over time in order to be durable.

An object of the invention is to provide a penile implant presenting a system for attachment to the pubic symphysis, designed so as not to lead to deterioration of the implant over time, even with intensive use.

In order to achieve such an object, the penile implant comprises an elongate erectile body supported by a symphyseal anchoring mount.

According to the invention, the symphyseal anchoring mount comprises a mounting plate presenting a bearing face extending in a plane and the erectile body extends from the face opposite the bearing face, in a direction that forms an angle of inclination with the plane of the bearing face, which angle lies in the range 5° to 30°, and preferably in the range 10° to 20°, the erectile body comprising at its end that is opposite the end provided with the symphyseal anchoring mount, a bulbous portion forming a glans.

In addition, the implant of the invention may further comprise in combination at least one and/or another of the following additional characteristics:

- the plate of the symphyseal anchoring mount includes through holes for an attachment system;
- the plate of the symphyseal anchoring mount comprises a mesh or a rigid insert, embedded in a silicone material;
- the erectile body is a malleable body formed by a silicone tube internally including a malleable core over a portion of its length;
- the malleable body is extended at one of its ends by the symphyseal anchoring mount while the other end of the malleable body is provided with a bulbous portion forming the glans;
- the bulbous portion is made by a removable hood that is fitted on the tube;
- the erectile body comprises at least one inflatable sealed tube designed to be connected to a reservoir and to an inflation pump, the tube being mounted on a receiving ferrule presented by the symphyseal anchoring mount;
- the ferrule of the symphyseal anchoring mount extends inside the tube over a portion of its length so as to support it in its deflated state; and
- the symphyseal anchoring mount comprises a connector fitting for a hydraulic fluid flow circuit, the connector fitting extending laterally while sloping towards the proximal end of the anchoring mount.

Various other characteristics appear from the following description given with reference to the accompanying drawings that show, as non-limiting examples, embodiments of the subject matter of the invention.

Figure 1:
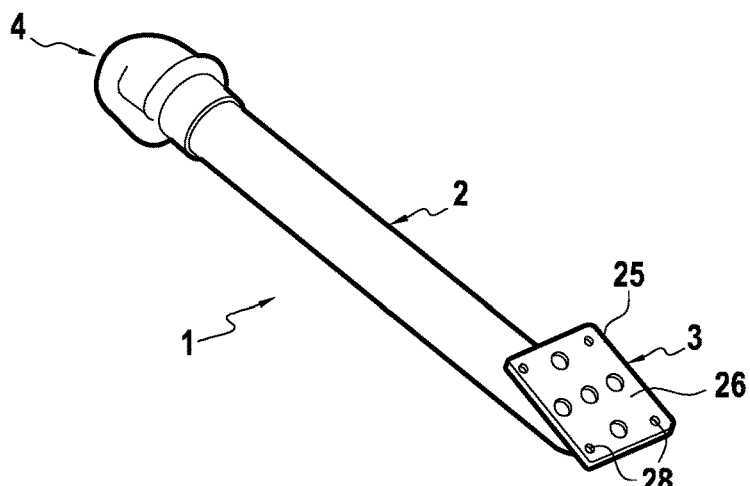
FIG. 1 is an elevation section view showing a first embodiment of a penile implant in accordance with the invention.

As can be seen more precisely from the figures, the subject matter of the invention relates to a penile implant for a female-to-male (FTM) transsexual. The penile implant 1 for an FTM transsexual is designed to create an erection in people having undergone phalloplasty.

The penile implant 1 comprises an erectile body 2 of elongate shape, supported by a symphyseal anchoring mount 3 for fixing on a person's pelvis. The erectile body 2 is thus provided at a first or "proximal" end, with the symphyseal anchoring mount 3.

In a preferred variant embodiment, the erectile body 2 includes a bulbous portion 4 forming the male glans. The erectile body 2 is thus provided at a second "distal" end, opposite the first, with a bulbous portion 4 reproducing the general shape of the glans.

In a first embodiment shown in FIGS. 1 to 4, the erectile body 2 is a malleable body formed by a silicone tube 6 internally including a malleable core 7 over a portion of its length. By way of example, the tube 6 has a diameter lying in the range 10 millimeters (mm) to 22 mm, while the malleable core 7 may be made by a length of multiple-twisted strands of metal inserted in the tube 6 and having a diameter in the range 2 mm to 4 mm. Such a malleable body may thus be deformed in particular in order to occupy a straight erection position and a drooping position.

According to a preferred embodiment characteristic, the malleable core 7 only occupies a fraction of the length of the tube 6 extending from the symphyseal anchoring mount 3. Thus, as can be seen more precisely in FIG. 3, the tube 6 presents between its distal end 6a and the end 7a of the malleable core 7, a portion of length L without a core that can be cut to size, allowing the tube to be shortened in order to adapt the implant to the size of the neo-penis. By way of example, the tube 6 has a length of 25 centimeters (cm) that is suitable for being shortened to a length of 12 cm for example.

In this embodiment, the tube 6 and the symphyseal anchoring mount 3 form a single part made using different manufacturing techniques such as molding, for example. In another embodiment, provision may be made to overmold the symphyseal anchoring mount 3 onto a reinforcement plate and then to adhesively bond it to the tube 6.

In this embodiment, the bulbous portion 4 is made in the form of a removable hood, fitted on the tube 6 at the "distal" end 6a of the tube, remote from the proximal end of the tube. This hood 4 is fastened on the distal end of the tube 6 by any appropriate means, e.g. by adhesive. By way of example, this hood 4 is made by molding and presents an anatomical shape that is analogous to the shape of the glans of a man. By way of example, this hood 4 presents a mounting ring 8 defining in part a blind housing 8₁ in which the distal end 6a of the tube 6 is engaged. This ring 8 is extended, opposite from its free edge, by an annular flange 9 from which there extends a pseudo-hemispherical cover 10.

FIGS. 5 to 8 show another embodiment of the erectile body 2 in the form of an inflatable body suitable firstly for being inflated to take up a straight erection position, and secondly for being deflated to take up a drooping position.

In this variant embodiment, the erectile body 2 is an elongate balloon, in the form of an inflatable sealed tube 11 connected to a reservoir and to an inflation pump, by a hydraulic fluid flow circuit. This tube 11, which is cylindrical in shape, defines a tubular sheath 12 beside the proximal end, which sheath is mounted on a receiving ferrule 13 presented by the symphyseal anchoring mount 3. The tube 11 is mounted on the symphyseal anchoring mount 3 in removable manner, or is fastened by any appropriate means. By way of example, the diameter of the tube 11 in the inflated state lies in the range 9 mm to 25 mm, while the size may vary in the range 12 cm to 25 cm. By way of example, the inflatable tube 11 is a single-layer tube made from a mixture of silicone and of polyurethane or from reinforced silicone (integrated mesh), or an assembly made from an inner silicone tube, an intermediate mesh reinforcement tube, and an outer silicone tube.

This tube 11 is closed in sealed manner at its distal end opposite from its proximal end, by a cap 14 fastened on the tube 11 by any appropriate means. Advantageously, the cap 14 is made to present the bulbous portion 4 forming the male glans. To this end, and as shown in the figures, the cap 14 is covered with a portion 15 of extra thickness provided at its free end with an annular flange 16 from which there extends a pseudo-hemispherical cover 17.

This tube 11 that is closed by the cap 14 thus forms an inflatable sealed body suitable for withstanding a pressure of 500 millibar (mbar) to 3 bars.

Figure 6:
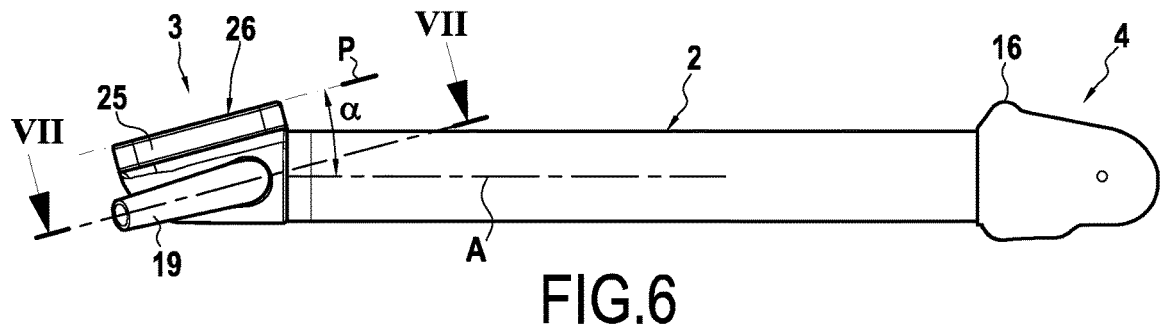
FIG. 6 is a side view showing the second embodiment of a penile implant in accordance with the invention.
Figure 7:
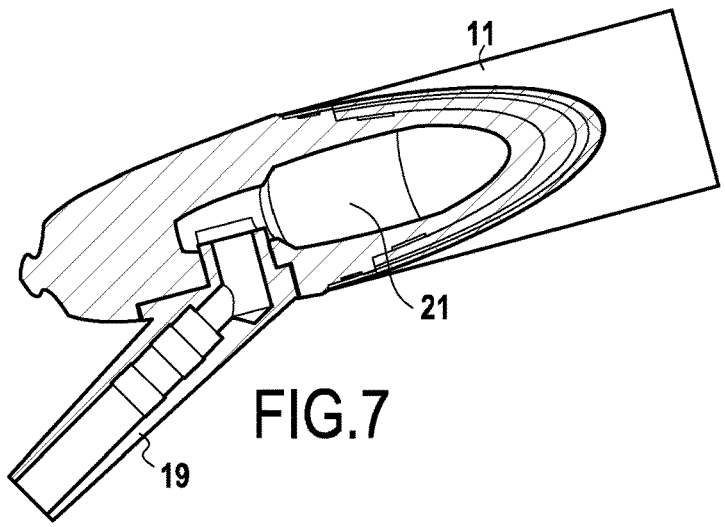
FIG. 7 is a cross-section taken substantially on lines VII-VII in FIG. 6 and showing a characteristic detail of the penile implant in accordance with the invention.
Figure 8:
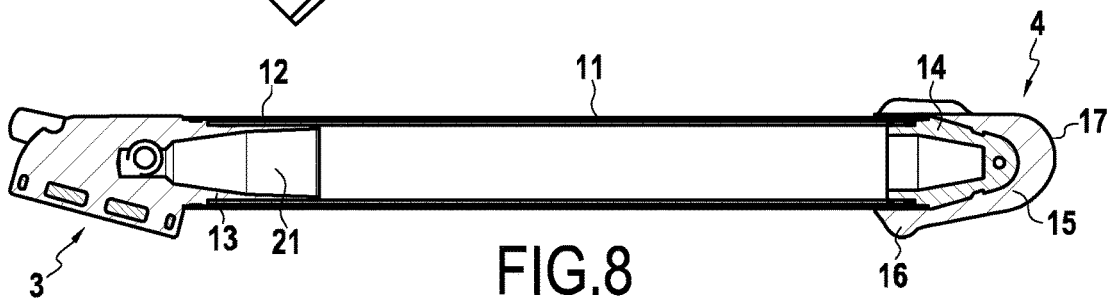
FIG. 8 is a longitudinal section view of the penile implant shown in FIGS. 5 and 6.

As can be seen more precisely in FIGS. 6 and 7, the symphyseal anchoring mount 3 includes a connector fitting 19 for a hydraulic fluid flow circuit (physiological saline solution) that is not shown. This fitting 19 enables the hydraulic fluid to flow between the inside of the inflatable body and the inflation pump, making it possible to inflate and deflate the sealed tube 11.

Figure 5:
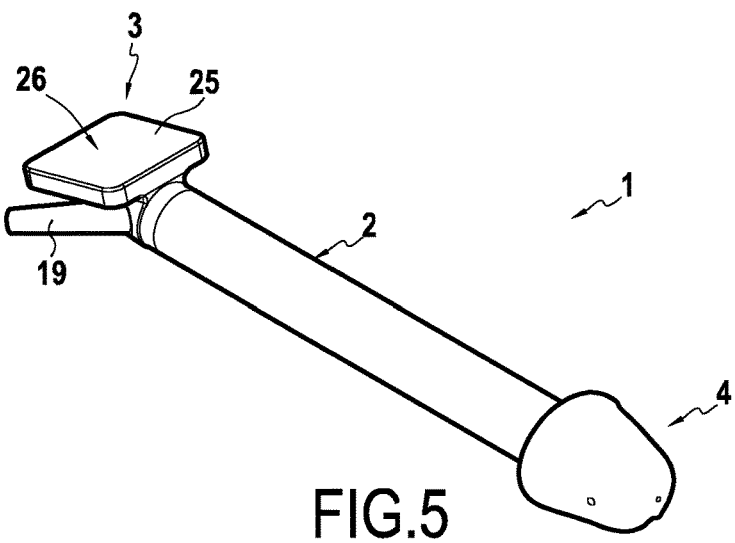
FIG. 5 is a perspective view showing a second embodiment of a penile implant in accordance with the invention.

In a preferred embodiment, the connector fitting 19 extends laterally, projecting relative to the symphyseal anchoring mount 3 and opening out into a chamber 21 provided in the symphyseal anchoring mount 3 and communicating at the ferrule 13 for mounting the tube 11. This connector fitting 19 extends while sloping towards the proximal end of the anchoring mount 3. By way of example, this connector fitting 19 forms an angle of the order of 30° with the longitudinal axis A of the implant. Advantageously, this connector fitting 19 projects from the right side of the anchoring mount when the fitting is placed in position on the patient, as can be seen in FIG. 5.

Such an arrangement makes it possible to position the hydraulic fluid flow circuit at a distance from the urethra and to avoid forming a bend that may potentially cause such a circuit to break.

According to an advantageous embodiment characteristic, the ferrule 13 of the symphyseal anchoring mount 3 forms a tongue that makes it possible to support the inflatable tube 11 when said tube is in its deflated position. This ferrule 13 extends inside the tube 11 from the symphyseal anchoring mount 3 over a portion of its length. When the tube 11 is deflated, this ferrule 13 enables the deflated body to be supported in an arcuate shape, preventing the tube from presenting a kink at the symphyseal anchoring mount 3.

Figure 2:
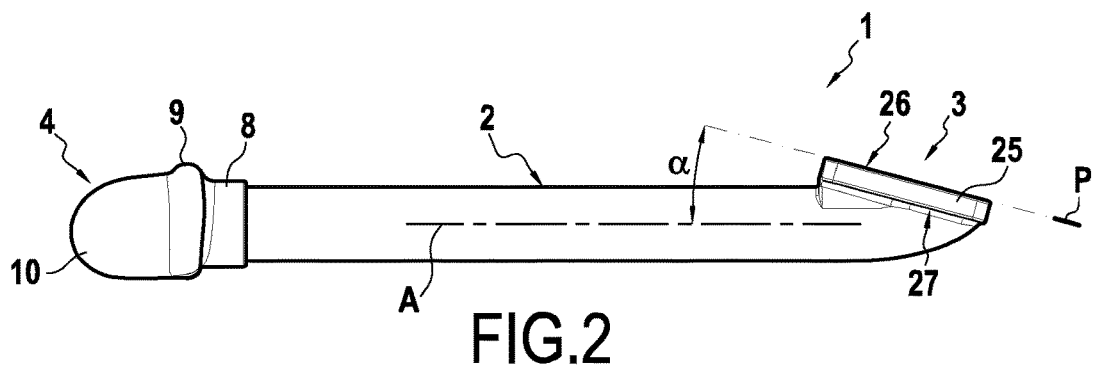
FIG. 2 is a side view showing the penile implant shown in FIG. 1.
Figure 3:
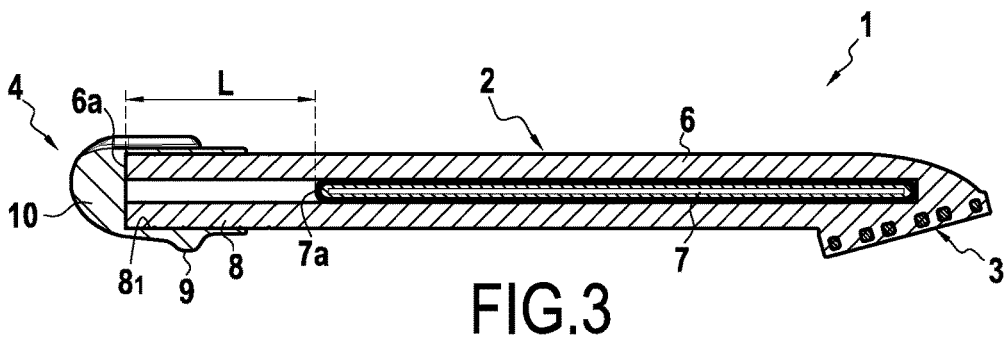
FIG. 3 is an elevation section view showing the penile implant shown in FIGS. 1 and 2.
Figure 4:
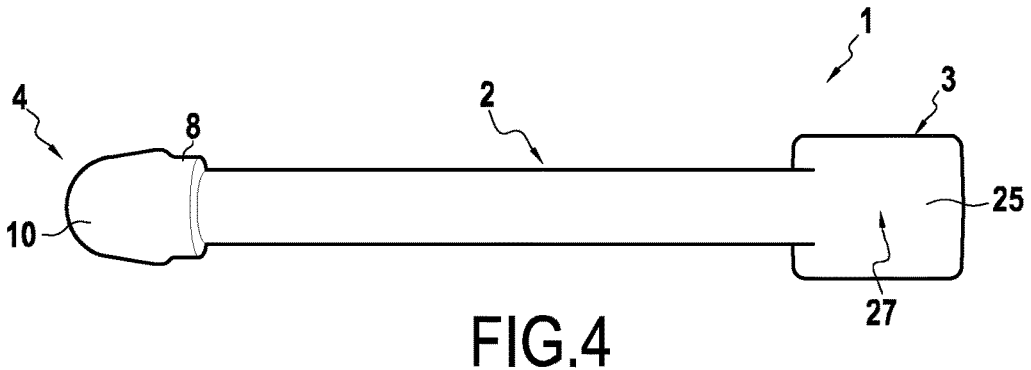
FIG. 4 is a side view showing the penile implant shown in FIGS. 1 to 3.

In accordance with the invention, the symphyseal anchoring mount 3 comprises a mounting plate 25 presenting a bearing face 26 extending in a plane P. This plane bearing face 26 is designed to come into contact with or to bear against the pubic symphysis or the anterior face of the pelvis. The mounting plate 25 thus presents the bearing face 26, on one side and an outer face 27 from which the erectile body 2 extends on its opposite side. According to a characteristic of the invention, the erectile body 2 extends from the face opposite the bearing face, in a direction A that forms an angle of inclination $\alpha$ with the plane of the bearing face 26, which angle of inclination $\alpha$ lies in the range 5° to 30° and preferably in the range 10° to 20°. The direction A of the erectile body 2 is considered when the body is in the erection position and is taken in a plane perpendicular to the plane P of the bearing face as can be seen in FIGS. 2 and 6.

The symphyseal anchoring mount 3 is fastened in any appropriate manner on the person's pelvis. In an embodiment that is shown more precisely in FIGS. 1 to 4, the plate 25 includes through holes 28 for an attachment system. The anchoring mount 3 can thus be fastened to the pelvis by means of anchoring screws or sutures passing through the holes 28 of the plate 25.

The plate 25 of the symphyseal anchoring mount 3 preferably comprises a rigid insert, such as a metal or polycarbonate plate, embedded in a silicone material. In another embodiment, the plate 25 of the symphyseal anchoring mount comprises a mesh embedded in a silicone material, possibly reinforced by an insert. In this example, the plate may be fastened by means of sutures cooperating with the mesh.

It can be seen from the above description that the penile implant 1 of the invention may be implanted easily and in the correct anatomical position given the presence of the symphyseal anchoring mount 3 and in particular of the mounting plate 25. In this position, the penile implant takes up an anatomical position that is ideal for absorbing the mechanical stresses to which the penile implant is subjected during use. The penile implant 1 of the invention makes it possible for phalloplasty (a simple sheath of skin grafted onto the pubis) to resemble the penis of a biological male, by reproducing the portions in relief of a natural penis and an erection. The penile implant of the invention thus constitutes a structure for covering, providing volume to the phalloplasty.

The invention is not limited to the examples described and shown since various modifications can be made without going beyond its ambit.

The invention claimed is:

1. A penile implant comprising an elongate erectile body supported by a symphyseal anchoring mount, comprising a mounting plate presenting a bearing face, the erectile body extending from the face opposite the bearing face, the implant being characterized in that the mounting plate extends in a plane and in that the erectile body extends in a direction that forms an angle of inclination with a plane of the bearing face, which angle lies in a range of from 5° to 30°, the erectile body comprising at its end that is opposite the end provided with the symphyseal anchoring mount, a bulbous portion forming a glans.

2. The penile implant according to claim 1, wherein the plate of the symphyseal anchoring mount includes through holes for an attachment system.

3. The penile implant according to claim 1, wherein the plate of the symphyseal anchoring mount comprises a mesh or a rigid insert, embedded in a silicone material.

4. The penile implant according to claim 1, wherein the erectile body is a malleable body formed by a silicone tube, internally including a malleable core over a portion of a length of the malleable body.

5. The penile implant according to claim 4, wherein the malleable body is extended at one of its ends by the symphyseal anchoring mount while the other end of the malleable body is provided with the bulbous portion forming the glans.

6. The penile implant according to claim 5, wherein the bulbous portion forming the glans is configured as a removable hood that is fitted on the erectile body.

7. The penile implant according to claim 1, wherein the erectile body comprises an inflatable sealed tube designed to be connected to a reservoir and to an inflation pump, the inflatable sealed tube being mounted on a receiving ferrule presented by the symphyseal anchoring mount.

8. The penile implant according to claim 7, wherein the ferrule of the symphyseal anchoring mount extends inside the inflatable sealed tube over a portion of a length of the inflatable sealed tube, so as to support the inflatable sealed tube in its deflated state.

9. The penile implant according to claim 7, wherein the symphyseal anchoring mount comprises a connector fitting for a hydraulic fluid flow circuit, the connector fitting extending laterally while sloping towards a proximal end of the symphyseal anchoring mount.

10. The penile implant according to claim 1, wherein the angle of inclination lies in a range of from 10° to 20°.

* * * * *